US011957908B1

(12) United States Patent
Alassiri et al.

(10) Patent No.: US 11,957,908 B1
(45) Date of Patent: Apr. 16, 2024

(54) DEVICE FOR ENHANCING MANDIBULAR BONE GROWTH

(71) Applicant: KING SAUD UNIVERSITY, Riyadh (SA)

(72) Inventors: Afnan Mohammad Alassiri, Riyadh (SA); Ali Mohamed Eltamaly, Riyadh (SA); Ali Awad Alrahlah, Riyadh (SA)

(73) Assignee: KING SAUD UNIVERSITY, Riyadh (SA)

( * ) Notice: Subject to any disclaimer, the term of this patent is extended or adjusted under 35 U.S.C. 154(b) by 0 days.

(21) Appl. No.: 18/485,667

(22) Filed: Oct. 12, 2023

(51) Int. Cl.
*A61N 2/00* (2006.01)
*A61N 1/36* (2006.01)

(52) U.S. Cl.
CPC ......... *A61N 1/36014* (2013.01); *A61N 2/004* (2013.01)

(58) Field of Classification Search
CPC ............. A61N 2/004; A61N 5/00; A61N 1/40
See application file for complete search history.

(56) References Cited

U.S. PATENT DOCUMENTS

| 6,443,883 B1 | 9/2002 | Ostrow et al. |
| 9,320,913 B2 | 4/2016 | Dimino et al. |
| 9,421,357 B2 | 8/2016 | Walker |
| 2011/0207990 A1* | 8/2011 | Mersky ................ H04R 25/554 381/151 |
| 2018/0001102 A1 | 1/2018 | Henry et al. |
| 2022/0203112 A1* | 6/2022 | Iger ........................ A61N 1/328 |

FOREIGN PATENT DOCUMENTS

| RU | 2153869 C1 | 10/2000 |
| RU | 2644925 C2 | 2/2018 |

OTHER PUBLICATIONS

Florian et al., "Use of Magnetic Neurostimulator Appliance in Temporomandibular Disorder," Journal of Acupuncture and Meridian Studies, vol. 10, Issue 2, Apr. 2017, pp. 104-108.

* cited by examiner

*Primary Examiner* — Mark W. Bockelman
(74) *Attorney, Agent, or Firm* — Nath, Goldberg & Meyer; Richard C. Litman

(57) ABSTRACT

A device for enhancing mandibular bone growth can include left and right head modules, a headband linking the left and right head modules and supporting the head modules, at least one transmitter circuit fixed to respective left and right head modules, left and right electrodes configured for receiving the transmitted electromagnetic field, and left and right transmitter antenna rods fixed to the left and right electrodes for receiving signals from the transmitter. The transmitter circuit can include a power supply, a driver, and at least one transmitter capable of transmitting an electromagnetic field for transmission to the patient's mandible.

8 Claims, 4 Drawing Sheets

DEVICE FOR ENHANCING MANDIBULAR BONE GROWTH

BACKGROUND

1. Field

The disclosure of the present patent application relates to a non-invasive device for temporomandibular stimulation and, more particularly, for generating a low-energy electromagnetic field for enhancing mandibular bone growth.

2. Description of the Related Art

Many conventional devices for treating an under-developed lower jaw and/or temporomandibular anomalies involve altering the electrical environment of tissue in an attempt to stimulate bone or tissue growth. These efforts typically concentrate on the use of electrode implants by which direct current can flow across or into a bone nonunion or abnormal union to stimulate repair of bone or articular cartilage. Due to numerous drawbacks, including the associated risks of surgery required to implant the electrodes, alternate, non-invasive techniques are desirable. While capacitively-generated electrostatic fields provide some beneficial results, the relatively large fields necessary are generally prohibitive.

Pulsed electromagnetic field (PEMF) therapy uses alternating electromagnetic fields to induce a voltage in bone. Non-invasive, non-thermal PEMF technologies have a long history of clinical use. Since the late 1990s, PEMF devices are estimated to have been used in over 3,000,000 treatments without reports of side effects or significant adverse events.

A meta-analysis conducted in 2018 examined the efficacy and safety of the pulsed electromagnetic field in osteoarthritis. The results showed that PEMF had significant effects in pain alleviation and function improvement compared with the sham-control group in patients with knee and hand osteoarthritis.

Another meta-analysis conducted in 2016 explored the Efficacy of Electrical Stimulators for Bone Healing. The findings resulting from this study support electrical stimulation as an adjunctive modality for radiographic bone healing and reduction in pain. For example, patients treated with electrical stimulation as an adjunct for bone healing had significantly less pain and experienced lower rates of radiographic nonunion or persistent nonunion.

A recent study exploring the effects of different PEMF treatment durations (ranging from 5 min to 60 min) over the mesenchymal stem cell (MSC) chondrogenic differentiation reported that the expression of MSC chondrogenic markers showed the greatest increase in response to 5 min to 20 min of PEMF treatment.

Thus, a device for enhancing mandibular bone growth solving the aforementioned problems is desired.

SUMMARY

A device for enhancing mandibular bone growth can include left and right head modules, a headband linking the left and right head modules, at least one transmitter circuit fixed to respective left and right head modules, left and right electrodes configured for receiving an electromagnetic field from a transmitter in the transmitter circuit, and left and right transmitter antenna rods fixed to the left and right head modules for receiving signals transmitted through the electrodes.

The headband can be positioned on a patient's head such that the antenna rods extend proximate the patient's mandible for transmitting signals received from the transmitter to the patient's mandible as an external electromagnetic field for absorption by the patient's mandible.

These and other features of the present subject matter will become readily apparent upon further review of the following specification.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1:
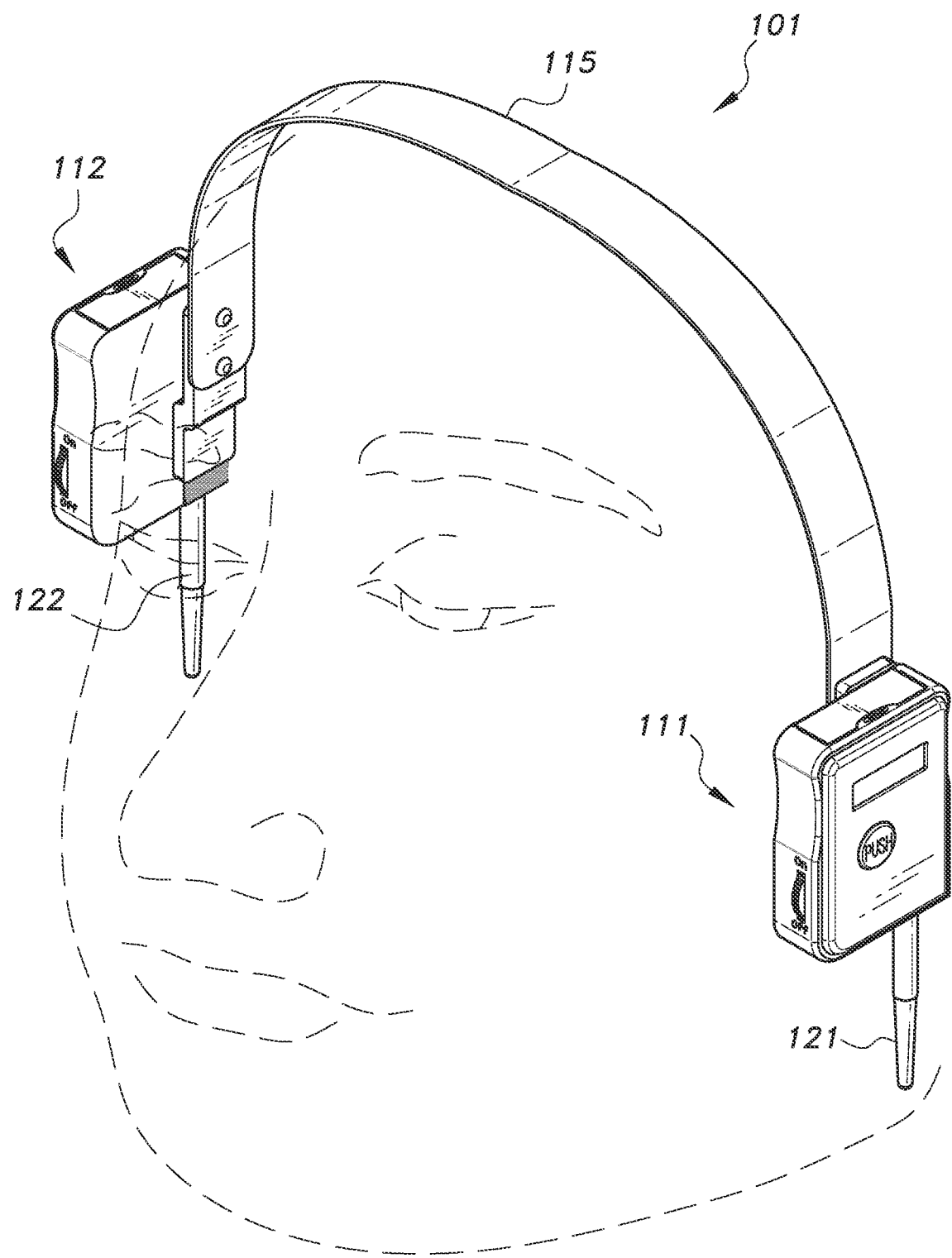
FIG. 1 is an environmental perspective view of a device for enhancing mandibular bone growth.

The present disclosure is related to a device for enhancing mandibular bone growth that can be worn by a patient to deliver an electromagnetic field to the condylar region and posterior border of the patient's mandibula. The device can include left and right head modules, a headband linking the left and right head modules, at least one transmitter circuit fixed to the respective left and right head modules, left and right electrodes configured for receiving an electromagnetic field transmitted by the circuit, and left and right transmitter antenna rods fixed to the left and right head modules for receiving signals from the electrodes. The transmitter circuit can include a power supply, a driver, and at least one transmitter capable of transmitting the electromagnetic field. A programmable controller controls the amplitude of current, pulse frequency, and duration of the electromagnetic field.

The headband can be positioned on a patient's head such that the antenna rods extend proximate the patient's mandible for transmitting signals received from the transmitter to the patient's mandible as an external electromagnetic field for absorption by the patient's mandible. The device can be useful for treating, for example, an underdeveloped lower jaw, temporomandibular anomalies, bone fractures, and post-surgical bone healing of the mandible. In particular, the device can be used to increase the vertical and anteroposterior dimensions of the lower jaw. The device can be used to enhance mandibular growth with or without a functional appliance for class II malocclusion.

The device can provide pulsed electromagnetic field (PEMF) therapy or generate electromagnetic waveform to stimulate bone growth. The headband can be generally U-shaped with each head module being disposed at a respective end of the headband and each of the antenna rods extending from a respective head module. One or both head modules can generate the PEMF that can be delivered to a fracture site through the antenna rods. The device is adapted to apply the PEMF to a predetermined location of the bone.

One or both head modules can include a controller that is programmable to regulate the amount of the wavelength applied to the targeted areas. The device also can be provided with a current interrupt mechanism for safety.

The headband can be worn on the head, similar to a head phone, such that the antenna rods are positioned proximate a desired area of treatment. This design ensures delivery of pulsed electromagnetic fields extra-orally to a target facial region without surgical intervention or intra-oral components. In addition, the headband is configured to be comfortable for the patient to wear, which is an important feature to ensure patient compliance with the treatment regimen.

The device can be used to treat certain orthodontic malocclusion, such as type 2 condylar hypoplasia due to mandibular deficiency or certain anomalies with condylar hypoplasia. Embodiments of the device can apply low energy to the tissues of the face and jaw with biologically effective pulsed field. Other aspects of the present subject matter provide methods for providing electromagnetic energy and methods for delivering the energy directly above the skin of a target area as a non-invasive method for treatment.

The present system can exert weak pulsing electrical current into particular anatomical areas of the face from outside of a patient's mouth. This technique may be used for treatment of condylar hypoplasia or stimulating mandibular bone growth and remodeling with or without conjunctional functional appliance to exert a force on maxillofacial bone, muscle, or soft tissue, or on one or more teeth of a patient. The device can generate a low-energy electromagnetic field on the temporomandibular region and posterior border of the mandible, muscle and soft tissue of the patient.

The device can induce a weak pulsing electrical current into a coil to generate electromagnetic waveform to a specific region. This current temporarily enhances bone growth in those areas. In an embodiment, the current can be delivered to selected areas in the condylar region and posterior border of the mandible where bone is forming. Significantly, the device can be worn externally, and provides a noninvasive feature, which is particularly advantageous when used in the face area.

The controller is configured to provide a voltage to the current to control one or more of energy density, pulse frequency, and duration of exposure. The pulsed electromagnetic field can be applied with a variable frequency and amplitude. Conceptually, the electromagnetic field induces microcurrents in the mandible to stimulate bone growth. Accordingly, the frequencies are selected to induce such microcurrents. By way of non-limiting example, the pulsed electromagnetic field has frequencies of about 100 Hz which can be applied for a few hours a day or more. In an embodiment, the pulsed electromagnetic field has a wide range of frequencies varying from 0.5 to 500 Hz. Most studies related osteoblast cells models rely on the 50-75 range of stimulation.

In an embodiment, a functional appliance can be employed to help reposition the mandibular bone in a forward and downward direction. Repositioning the mandibular bone forward can create muscle tension on the joint area of the mandibular bone. This tension or force can stimulate osteoblastic activity or bone remodeling, which can lengthen the mandibular bone through bone deposition on the condylar head and glenoid fossa of the temporal bone of the skull. The force can be applied subsequent to, concurrently with, or prior to administration of PEMF. The electromagnetic waveform generates a stray current around the bone which provides a potential in stimulating condylar growth.

Figure 2A:
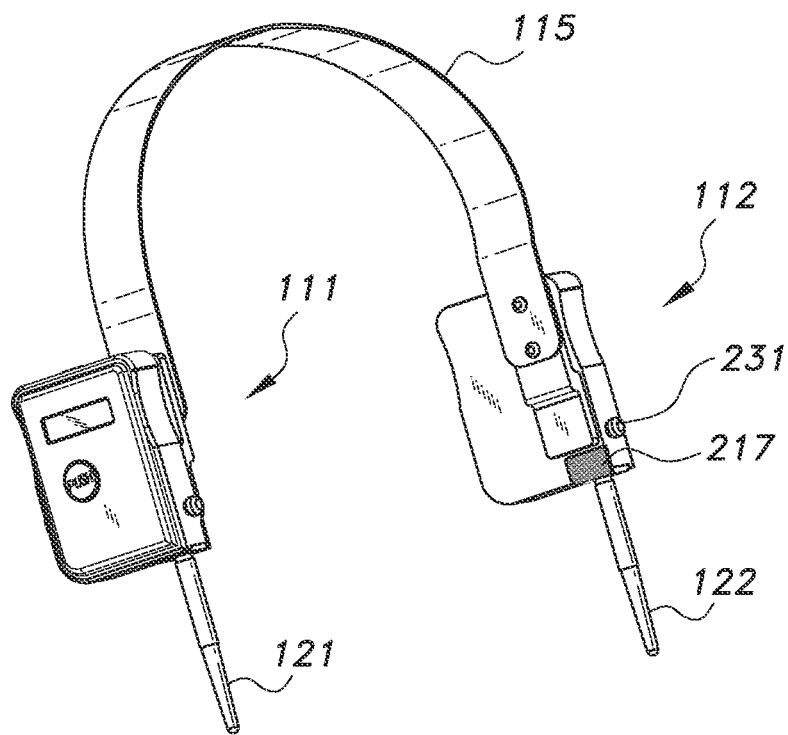
FIG. 2A is a perspective view of one of the head modules of the appliance of FIG. 1.
Figure 2B:
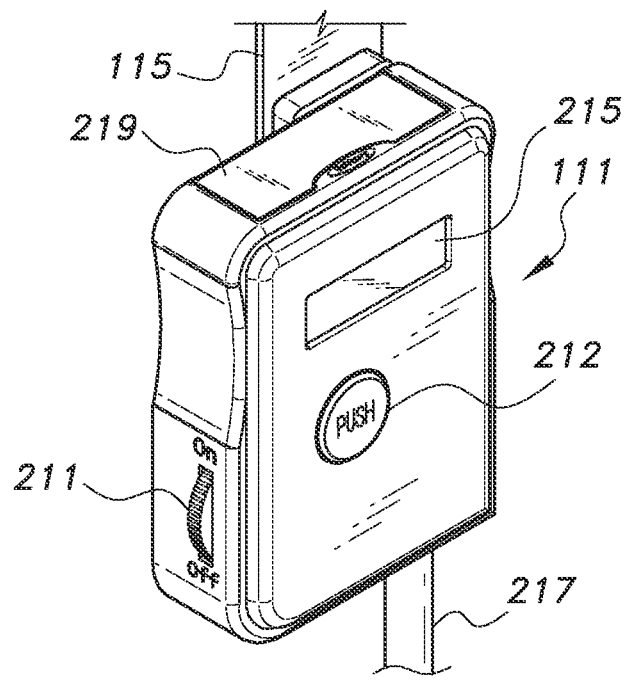
FIG. 2B is an enlarged view of one side of the head module depicted in FIG. 2A, showing details thereof.
Figure 2C:
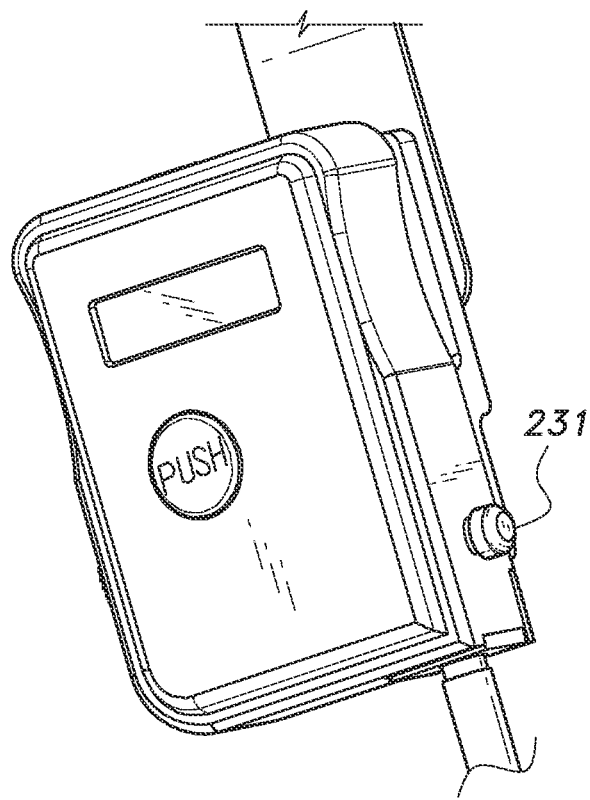
FIG. 2C is an enlarged view of another side of the head module depicted in FIG. 2A, showing details thereof.
Figure 2D:
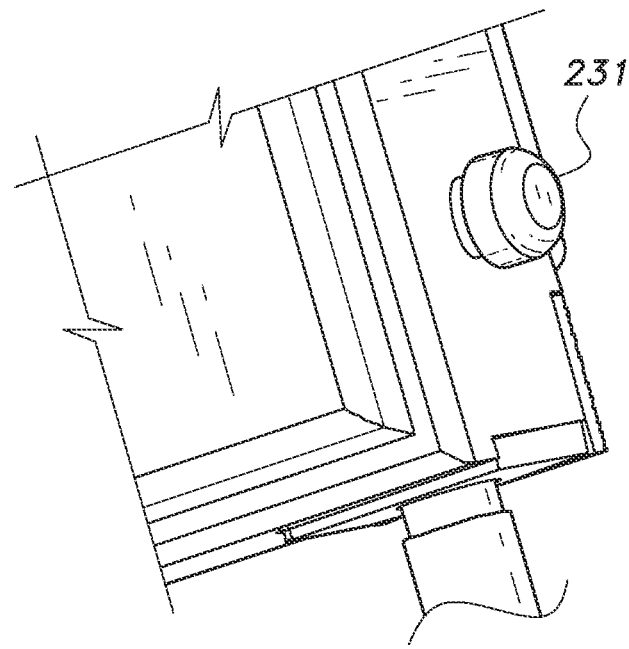
FIG. 2D is an enlarged view of a lower corner of the head module depicted in FIG. 2C.

FIG. 1 shows an environmental view of the device for enhancing mandibular bone growth 101. Depicted are left and right head modules 111, 112 linked by headpiece 115. As shown in FIGS. 2A-2B, antenna rods 121, 122 extend from left and right head modules 111, 112. Electrodes 217 are affixed to a respective head module 111, 112. Also shown is Rx order key 231, which provides or locks in a desired pattern of electromagnetic energy transmitted by the device 101 when the device 101 is turned on.

When the headpiece 115 is placed on the patient's head, antenna rods 121, 122 can be disposed adjacent the patient's mandible to transmit electromagnetic energy to the mandible. Antenna rods 121, 122 can include loading coils to provide an effective length for transmission; e.g., ¼λ for each rod or ¼λ as a single combined antenna. As such, antenna rods 121, 122 can be provided as anatomically configured treatment coils. In an embodiment, antenna rods 121, 122 are configured to be extendible.

FIGS. 2A-2D provide details of one of the head modules 111. It should be understood that head module 112 is identical to head module 111. Head module 111 includes a case 208, power switch 211, operating button 212, display screen 215 and electrode 217. A battery (not shown) is accessed through battery door 219.

In operation, one or both head modules 111, 112 generate electromagnetic energy, which is transmitted through electrodes 217 from both head modules 111, 112 to the respective antenna rods 121, 122. Each module 111, 112 may have separate transmitters, or a single transmitter in one head module can transmit the electromagnetic energy across headband 115 to the other head module.

A method for enhancing mandibular bone growth can include administering an electromagnetic field to an area along the patient's posterior jaw line to stimulate bone growth in a target area, e.g., the condylar region and posterior border of the mandibula which are responsible for increasing the vertical and anteroposterior dimensions of the lower jaw. This can be used with or without a functional appliance to help in repositioning the mandibular bone in a forward and downward direction. Repositioning a mandibular bone forward can create muscle tension on the joint area of the mandibular bone or other parts of the mandibular bone. This tension or force can stimulate osteoblastic activity or bone remodeling, which can lengthen the mandibular bone through bone deposition on the condylar head and glenoid fossa of the temporal bone of the skull. This force can be applied subsequent to, concurrently with, or prior to the administration of pulsed electromagnetic field (PEW') therapy.

The controller can be programmed to control the transmitter circuit and provide instructions to the programmable driver circuit for a treatment regimen (herein, "Treatment Rx"). The controller can control the amplitude of current, pulse frequency, and duration of the external electromagnetic field therapy device. The programmable controller can generate an electromagnetic field at the predetermined rates and frequencies onto the treatment area. The device is configured to generate a signal to remind a patient of at least one of the scheduled treatments, and to provide effective, stabilized, repeatable, accurate, programmable, and consistent energy therapy for the treatment and stimulation of soft and hard tissue and the stimulation of bone. The device can be programmed to give instructions for a treatment regimen by electronic communication such as Bluetooth or USB connections or by the insertion of Rx order key 231. Rx order key 231 can alternatively lock the instructions programmed by other means. The key 231 can be used for activating the controller in the device 10. Treatment Rx orders can be displayed on display screen 215. Operating button 212 is described by way of non-limiting example, as any circuit capable of controlling and programming the electromagnetic output. Other examples include a USB connection, Bluetooth or other radio connections or other physical connections. On a basic level, the control and programming can be achieved in a manner such as used by TENS units, which can be by manual control or by programming. The device can include an emergency switch that can monitor and deactivate both devices if the current changes suddenly or if one of the head modules is not working appropriately.

According to an embodiment, a length of the headband 115 can be adjusted. The length of the antenna rods 121, 122 can also be adjustable to accommodate the dimensions of the patient's mandible and of the targeted area of the mandible.

When antenna rods 121, 122 are placed near or against the patient's skin adjacent to the tissues desired to be treated, electromagnetic fields extend to the area of treatment. Antenna rods 121, 122 can be replaced with different length rods as needed to reach a posterior border of the mandible.

In operation, a programmable controller controls the amplitude of current, pulse frequency and duration of the external electromagnetic field therapy device. The programmable controller runs a patient's prescribed treatment regimen (Rx order), causing the generation of electromagnetic fields at the predetermined rates and frequencies onto the treatment area. The device can be programmed to generate a signal to remind a patient of at least one of the scheduled treatments. The electromagnetic field device can provide effective, stabilized, repeatable, accurate, programmable, and consistent energy therapy for the treatment and stimulation of soft and hard tissue and the bio-stimulation of bone.

Figure 3:
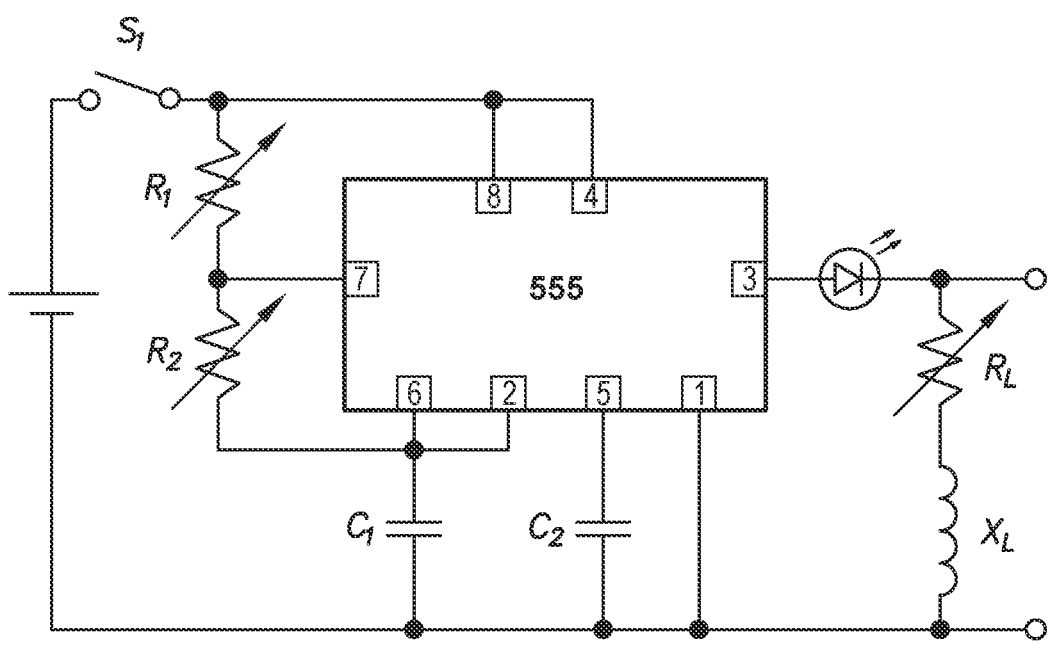
FIG. 3 is a schematic diagram of a signal generator used to generate a waveform for administration of pulsed electromagnetic field (PEMF) therapy.

As the disclosed technique is used to enhance mandibular growth with or without a functional appliance for class II malocclusion in the face area, this is accomplished non-invasively by use of PEMF. There are many signal generators that can be used to generate this waveform. In the disclosed technique a simple and effective electric circuit has been developed to generate this signal. FIG. 3 is a schematic diagram showing a non-limiting example of a circuit using an IC555 timer integrated circuit to generate this signal. This chip is commonly used for controlling devices and is suitable for controlling the transmitter. The IC555 can generate a frequency output in a wide range (from a few hertz to 500 kHz), and operates with a low current draw, typically less than 1 mA which can prolong battery life. The output frequency can be controlled by controlling R1, R2 using the following equation:

$$\text{frequency} = \frac{1}{C_1(R_1 + 2R_2)}$$

The circuit can include an elapsed real-time clock that measures the total time the device 101 is used.

It is to be understood that the device for enhancing mandibular bone growth is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. A device for enhancing mandibular bone growth, comprising:
    left and right head modules;
    a headband linking the left and right head modules, the head band being configured to be worn on the head of a user;
    at least one transmitter circuit fixed to respective ones of the left and right head modules, the transmitter circuit comprising a power supply, a driver and at least one transmitter for transmitting an electromagnetic field;
    left and right electrodes connected to respective left and right head modules, the electrodes being configured for receiving the transmitted electromagnetic field; and
    left and right transmitter antenna rods fixed to the respective left and right head modules and configured for receiving signals through the respective electrodes from the transmitter, and transmitting the received signals from the transmitter to the patient's mandible as an external electromagnetic field for absorption by the patient's mandible.

2. The device for enhancing mandibular bone growth as described in claim 1, further comprising:
    a programmable controller capable of controlling the driver and transmitter; and
    a program control input providing control instructions to the programmable driver circuit.

3. The device for enhancing mandibular bone growth as described in claim 1, further comprising:
    a programmable controller configured to control the amplitude of current, pulse frequency and duration of the electromagnetic field.

4. The device for enhancing mandibular bone growth as described in claim 3, wherein the programmable controller controls transmission of the electromagnetic field to provide pulsed electromagnetic field (PEMF) therapy by transmitting the electromagnetic field at frequencies ranging from 0.5 Hz to 500 kHz.

5. A method for non-invasively providing electrostimulation to a patient's mandible, comprising:
    providing the device of claim 1;
    transmitting an electromagnetic field to the patient's mandible as an external electromagnetic field for absorption by the patient's mandible, through left and right transmitter antenna rods fixed to the left and right head modules; and
    controlling the transmission of the electromagnetic field to achieve pulsed electromagnetic field (PEMF) therapy by transmitting the electromagnetic field at frequencies ranging from 0.5 Hz to 10 kHz.

6. The method of claim 5, further comprising:
    controlling the transmission of the electromagnetic field to provide the PEMF therapy by transmitting the electromagnetic field at frequencies ranging from 2 Hz to 500 Hz.

7. The method of claim 5, further comprising:
    using the programmable controller to control the transmitter circuit; and
    providing control instructions to the programmable driver circuit.

8. The method of claim 7, further comprising:
using the programmable controller to control the amplitude of current, pulse frequency and duration of the external electromagnetic field.

* * * * *